(12) United States Patent
Neas et al.

(10) Patent No.: US 9,877,483 B2
(45) Date of Patent: Jan. 30, 2018

(54) COMPOSITIONS COMPRISING PEROXYACID AND METHODS FOR PRODUCING AND USING THE SAME

(71) Applicant: CHD Bioscience, Inc., Ft. Collins, CO (US)

(72) Inventors: Edwin D. Neas, Nunn, CO (US); John D. Skinner, Fort Collins, CO (US)

(73) Assignee: Armis Biopharma, Inc., Fort Collins, CO (US)

( * ) Notice: Subject to any disclaimer, the term of this patent is extended or adjusted under 35 U.S.C. 154(b) by 0 days.

(21) Appl. No.: 15/403,842

(22) Filed: Jan. 11, 2017

(65) Prior Publication Data

US 2017/0118991 A1    May 4, 2017

Related U.S. Application Data

(63) Continuation of application No. 14/058,124, filed on Oct. 18, 2013, now abandoned.

(60) Provisional application No. 61/715,725, filed on Oct. 18, 2012.

(51) Int. Cl.
*A61K 31/22* (2006.01)
*A61K 33/40* (2006.01)
*A01N 59/00* (2006.01)
*A01N 37/42* (2006.01)

(52) U.S. Cl.
CPC .............. *A01N 59/00* (2013.01); *A01N 37/42* (2013.01); *A61K 31/22* (2013.01); *A61K 33/40* (2013.01)

(58) Field of Classification Search
USPC ........................................................ 514/557
See application file for complete search history.

(56) References Cited

U.S. PATENT DOCUMENTS

| | | | |
|---|---|---|---|
| 2,806,045 A | 9/1957 | Gross |
| 3,169,986 A | 2/1965 | Webb et al. |
| 3,829,468 A | 8/1974 | Serad et al. |
| 3,978,032 A | 8/1976 | Manner |
| 4,004,977 A | 1/1977 | Kato et al. |
| 4,008,175 A | 2/1977 | Barter |
| 4,051,059 A | 9/1977 | Bowing et al. |
| 4,743,447 A | 5/1988 | Le Rouzic et al. |
| 5,437,868 A | 8/1995 | Oakes et al. |
| 5,508,046 A | 4/1996 | Cosentino et al. |
| 5,597,791 A | 1/1997 | Richards et al. |
| 5,718,910 A | 2/1998 | Oakes et al. |
| 6,325,968 B1 | 12/2001 | Fricker et al. |
| 6,627,594 B1 | 9/2003 | James et al. |
| 6,627,657 B1 | 9/2003 | Hilgren et al. |
| 6,943,190 B2 | 9/2005 | Fink et al. |
| 6,991,685 B2 | 1/2006 | Kravitz et al. |
| 8,349,449 B2 | 1/2013 | Privitera et al. |
| 8,426,634 B2 | 4/2013 | Neas et al. |
| 8,445,717 B2 | 5/2013 | Neas et al. |
| 2001/0016604 A1 | 8/2001 | Yu et al. |
| 2004/0176267 A1 | 9/2004 | Hobson et al. |
| 2005/0197397 A1 | 9/2005 | Martin |
| 2007/0048345 A1 | 3/2007 | Huang et al. |
| 2007/0056904 A1 | 3/2007 | Hogt et al. |
| 2007/0082832 A1 | 4/2007 | DiCosimo et al. |
| 2007/0148214 A1 | 6/2007 | Cullen et al. |
| 2007/0202069 A1 | 8/2007 | Tamareselvy et al. |
| 2007/0239947 A1 | 10/2007 | Li et al. |
| 2008/0233069 A1 | 9/2008 | Tamareselvy et al. |
| 2009/0010998 A1 | 1/2009 | Marchitto et al. |
| 2009/0061017 A1 | 3/2009 | Pedersen et al. |
| 2009/0145859 A1 | 6/2009 | Man et al. |
| 2009/0269324 A1 | 10/2009 | Herdt et al. |
| 2010/0040608 A1 | 2/2010 | Wahren-Herlenius et al. |
| 2010/0108942 A1 | 5/2010 | Man et al. |
| 2010/0125104 A1 | 5/2010 | Neas et al. |
| 2010/0326217 A1 | 12/2010 | Takahashi et al. |
| 2011/0117178 A1 | 5/2011 | Junginger |
| 2011/0165261 A1 | 7/2011 | Derby et al. |
| 2011/0301070 A1 | 12/2011 | Ochomogo et al. |
| 2011/0305872 A1 | 12/2011 | Li et al. |
| 2012/0021486 A1 | 1/2012 | Dinu et al. |
| 2012/0213835 A1 | 8/2012 | Neas et al. |
| 2013/0224307 A1 | 8/2013 | Neas et al. |

(Continued)

FOREIGN PATENT DOCUMENTS

| | | |
|---|---|---|
| CN | 2346414 Y | 11/1999 |
| CN | 1543795 A | 11/2004 |
| EP | 0 320 219 A1 | 6/1989 |

(Continued)

OTHER PUBLICATIONS

Turćić et al., "Peroxyacetic Acid Effect on the Bacteriologic Status of War Wound," Acta Med. Croatica, 51 (1997) 159-162.

(Continued)

*Primary Examiner* — Walter Webb
(74) *Attorney, Agent, or Firm* — Volpe and Koenig, P.C.

(57) ABSTRACT

The present invention provides methods for producing a non α-keto peracid that has lower toxicity and lower corrosivity. The present embodiments also provide methods and compositions for reducing microbes on a surface, methods, and compositions for preventing and reducing infectious vegetative bacteria on a substrate, and methods and compositions for treating a wound. In particular, compositions of the invention provide for a mixture of an α-keto peracid and a non α-keto peracid that works synergistically to reduce microbes on a surface, to prevent vegetative bacteria on a surface and to heal a wound in animals or humans.

22 Claims, 7 Drawing Sheets

(56) References Cited

U.S. PATENT DOCUMENTS

| | | | |
|---|---|---|---|
| 2013/0251820 A1 | 9/2013 | Neas et al. | |
| 2013/0330397 A1 | 12/2013 | Neas et al. | |

FOREIGN PATENT DOCUMENTS

| | | | |
|---|---|---|---|
| JP | 2002-045419 A | 2/2002 | |
| JP | 2003-038633 A | 2/2003 | |
| KR | 20 0390463 Y1 | 7/2005 | |
| WO | 91/13058 A1 | 9/1991 | |
| WO | 93/01716 A1 | 2/1993 | |
| WO | 2006/093792 A1 | 9/2006 | |
| WO | 2007/018923 A1 | 2/2007 | |
| WO | 2010/059531 A1 | 5/2010 | |
| WO | 2011/129829 A1 | 10/2011 | |
| WO | 2012/112951 A1 | 8/2012 | |

OTHER PUBLICATIONS

Mullen, "Disinfectants and Public Health Biocides," The Biocides Business: Regulation, Safety and Applications (2002) 251-266.
Material Safety Data Sheet Hydrogen Peroxide Solution MSDS—Hydrogen Peroxide Solutions (2011).
Tong et al., "Preparation and properties of pullulan-alginate-carboxymethylcellulose blend films," Food Research International 41 (2008) 1007-1014.
Chen et al., Extracellular HMGB1 as a Proinflammatory Cytokine, Journal of Interferon & Cytokine Research, 24:329-33 (2004).
International Search Report for PCT/US13/65769 dated Apr. 17, 2014, 46 pages.
Bunton (1949) Nature 163:444 "Oxidation of a-Diketones and a-Keto-Acids by Hydrogen Peroxide".
Cooper, et al. (1983) Chem. Rev. 83:321-358 "Synthesis and Properties of the a-Keto Acids".
Desagher et al. (1997) The Journal of Neuroscience 17(23):9060-9067 "Pyruvate Protects Neurons against Hydrogen Peroxide-Induced Toxicity".
Estes et al. (2010) Expert Rev Anti Infect Ther 8(3):325-338 "Present and future therapeutic strategies for melioidosis and glanders" doi:10.1586/eri.10.4.
European Search Report for 09828061.3 dated Sep. 24, 2012, 7 pages.
Fink (2003) J Trauma Injury Infection Critical Care 54:S 141-S 143 "Ringer's Ethyl Pyruvate Solution: A Novel Resuscitation Fluid for the Treatment of Hemorrhagic Shock and Sepsis".
Fink (2007) Current Drug Targets 8:515-518 "Ethyl Pyruvate: A Novel Treatment for Sepsis".
Fink (2007) J Intern Med 261:349-362 "Ethyl pyruvate: a novel anti-inflammatory agent".
Greenspan (1947) Industrial and Engineering Chemistry 39:847-848 "Oxidation Reactions C9 with Aliphatic Peracids" XP-002683108.
Hanson (1987) Department of Biological Sciences 64(7):591-595 "Decarboxylation of a-Keto Acids".
Holleman (1904) Reel. Trav. Chim. Pays-bas Belg. 23 (English Abstract).
International Search Report for PCT/US09/64450 dated May 31, 2010, 5 pages.
International Search Report for PCT/US10/31245 dated Jan. 21, 2011, 5 pages.
International Search Report for PCT/US12/25736 dated May 29, 2012, 1 page.
International Search Report for PCT/US13/54968 dated Jan. 14, 2014, 20 pages.
International Search Report for PCT/US13/65782 dated Feb. 19, 2014, 32 pages.
Lever and Mackenzie (2007) BMJ 335:879-883 "Sepsis: definition, epidemiology, and diagnosis".
Miyaji et al. (2003) Kidney International 64:1620-1631 "Ethyl pyruvate decreases sepsis-induced acute renal failure and multiple organ damage in aged mice".
Nath et al. (1995) The American Physiological Society C227-C236 "a-Ketoacids scavenge H2O2 in vitro and in vivo and reduce menadione-induced DNA injury and cytotoxicity".
Neas et al. (2013) Power Point Presentation presented on Jan. 3, 2013 for U.S. Appl. No. 12/618,605 "CHD Bioscience: Answers for infectious disease: CHD Meeting with USPTO" 31 slides.
North Cell Pharm pamphlet "Effect of Alpha Keto Acids Including Sodium Pyruvate on Reducing and Regulating the Inflammatory Agents Needed in the Healing of Infected and Non-Infected Wounds" [retrieved on Jan. 29, 2014 from http://www.northcellpharma.com/NCP Research Devel Data. pdf].
Panda and Patnaik (2001) Bull. Korean Chern. Soc. 22(8):909-913 "Peroxy Acid Oxidations: A Kinetic and Mechanistic Study of Oxidative Decarboxylation of a-Keto Acids by Peroxomonophosphoric Acid".
Swern (1948) Eastern Regional Research Laboratory 1-68 "Organic Peracids".
Vlachou and Berth-Jones (2007) Journal of Dermatological Treatment 18:175-177 "Nail psoriasis improvement in a patient treated with fumaric acid esters".
Vlessis et al. (1990) Biochemical and Biophysical Research Communications 170(3): 1281-1287 "Importance of Spontaneous a-Ketoacid Decarboxylation in Experiments Involving Peroxide".
Wang et al. (1999) Science 285:248-251 "HMG-1 as a Late Mediator of Endotoxin Lethality in Mice".

| Pathogen | Type | Log 10 Kill | Time to Kill | Composition ppm |
|---|---|---|---|---|
| E. Coli | Bacteria | ≥ 6 | ≤ 15s | 2,000 |
| MRSA | Bacteria | ≥ 6 | ≤ 15s | 2,000 |
| P. aerginosa | Bacteria | ≥ 6 | ≤ 1m | 500 |
| A. baumannii | Bacteria | ≥ 6 | ≤ 15s | 100 |
| B. pseudomallei | Bacteria | ≥ 6 | ≤ 1m | 50 |
| M. massilliense | Mycobacteria | ≥ 7 | ≤ 5m | 1,000 |
| M. chelone | Mycobacteria | ≥ 7 | ≤ 15m | 1,000 |
| M. bovis | Mycobacteria | ≥ 7 | ≤ 1m | 1,000 |
| M. avium | Mycobacteria | ≥ 7 | ≤ 15m | 1,000 |
| M. terrae | Mycobacteria | ≥ 7 | ≤ 5m | 1,000 |
| M. tuberculosis | Mycobacteria | ≥ 7 | ≤ 5m | 1,000 |
| C. albicans | Fungus | ≥ 6 | ≤ 15s | 100 |
| Aspergillus genus | Fungus | ≥ 6 | ≤ 10m | 3,500 |
| Influenza genus | Virus | ≥ 5 | ≤ 1m | 300 |
| C. difficile | Spores | ≥ 6 | ≤ 5m | 1,500 |
| B. subtillis | Spores | ≥ 5 | ≤ 10m | 4,000 |

FIG. 5A

| Pathogen | Time | Log Reduction* | Concentration |
|---|---|---|---|
| S. aureus | 15 sec | >4.2 | 250ppm |
| E. coli | 15 sec | >4.7 | 250ppm |
| MRSA | 30sec | >5.0 | 250ppm |
| A. baumanii | 30sec | >5.7 | 250ppm |
| K. pneumoniae | 30sec | >4.1 | 1,000ppm |
| P. aeruginosa | 30sec | >3.9 | 1,000ppm |
| B. subtilis spores | 3min | >3.2 | 2,300ppm |
| B. cereus spores | 3min | >3.7 | 2,300ppm |
| C. difficile spores | 30 sec | >4.7 | 2,500ppm |

FIG. 5B

COMPOSITIONS COMPRISING PEROXYACID AND METHODS FOR PRODUCING AND USING THE SAME

CROSS REFERENCE TO RELATED APPLICATION

This application is a continuation of U.S. patent application Ser. No. 14/058,124, which was filed Oct. 18, 2013, and claims priority to U.S. Provisional Patent Application No. 61/715,725, filed Oct. 18, 2012, both of which are incorporated herein by reference as if fully set forth.

TECHNICAL FIELD

The present invention relates to compositions comprising peroxycarboxylic acids and methods for producing and using the same.

BACKGROUND

The skin is the body's largest organ and serves as the primary protective barrier to the outside world. Any physical disruption (i.e., wound) to this organ must therefore be quickly and efficiently repaired in order to restore tissue integrity and function. Quite often proper wound healing is impaired with devastating consequences such as severe morbidity, amputations, or death. In humans and animals, protection from mechanical injury, chemical hazards, and bacterial invasion is provided by the skin because the epidermis is relatively thick and covered with keratin. Secretions from sebaceous glands and sweat glands also benefit this protective barrier. In the event of an injury that damages the skin's protective barrier, the body triggers a wound healing cascade of events.

The classical model of wound healing is divided into three or four sequential, yet overlapping, phases: (1) hemostasis, (2) inflammatory, (3) proliferative and (4) remodeling. The hemostasis phase involves platelets (thomboctytes) to form a fibrin clot to control active bleeding. The inflammatory phase involves migration of phagocytes to the wound to kill microorganisms and release of subsequent signaling factors to involve the migration and division of cells involved in the proliferative phase. The proliferative phase involves vascular cell production for angiogenesis, fibroblast cells to excrete collagen and fibronectin to form an extracellular matrix, and epithelial cells to reform the external epidermis. In addition, the wound is made smaller by myofibroblasts. Finally, collagen is remodeled and cells that are no longer needed are removed by programmed cell death (i.e., apoptosis).

The process of wound healing can be divided into two major phases: early phase and cellular phase. See FIG. 1. The early phase involves hemostasis which involves vasoconstriction, temporary blockage of a break by a platelet plug, and blood coagulation, or formation of a clot that seals the hole until tissues are repaired. The early phase also involves the generation of stimuli to attract the cellular responses needed to instigate inflammation. In the inflammation phase (see FIG. 2), white blood cells, or leukocytes, are attracted to the wound site by platelet-derived growth factor (PDGF), and these cells of the immune system are involved in defending the body against both infectious disease and foreign materials. There are 18 other known proteins involved in the inflammatory phase which interact to regulate this response. For example, IL-4, IL-10, and IL-13 are potent activators of B lymphocytes. However, IL-4, IL-10, and IL-13 are also potent anti-inflammatory agents. The phagocytic cells engulf and then digest cellular debris and pathogens and stimulate lymphocytes and other immune cells to respond to the wound area. Once the invading microorganisms have been brought under control, the skin proceeds through the proliferative and remodeling stage by a complex cascade of biochemical events orchestrated to repair the damage. This involves the formation of a scab within several hours. The scab temporarily restores the integrity of the epidermis and restricts the entry of microorganisms. After the scab is formed, cells of the stratum basale begin to divide by mitosis and migrate to the edges of the scab. A week after the injury, the edges of the wound are pulled together by contraction. Contraction is an important part of the healing process when damage has been extensive, and involves shrinking in size of underlying contractile connective tissue, which brings the wound margins toward one another. In a major injury, if epithelial cell migration and tissue contraction cannot cover the wound, suturing the edges of the injured skin together, or even replacement of lost skin with skin grafts, may be required to restore the skin. Interruption of this healing process by a breakdown in any of these wound healing processes will lead to a chronic wound.

Other skin wounds involve burns. Major burns are relatively common injuries that require multidisciplinary treatment for patient survival and recovery. More than 30,000 people the each year worldwide because of fire-related burn injuries. Many more are seriously injured, disabled, or disfigured because of all types of burns. There have been significant advances in medical care for burns over the last 15 years due to fluid resuscitation, wound cleaning, skin replacement, infection control, and nutritional support. These changes have primarily resulted from the use of early burn wound excursion, early adequate nutrition, and the use of surgical techniques that minimize blood and heat loss. Since modern treatment of burns has greatly advanced, sepsis has become the leading cause of death after a burn injury. Multiple antibiotic resistant bacteria and fungus now account for the bulk of deaths due to sepsis in burns, the etiology of which is due to antibiotic resistant bacteria and biofilm formation in the wound and extraneous nosocomial infections.

Impediments to wound healing include hypoxia, infection, presence of debris and necrotic tissue, use of inflammatory medications, a diet deficient in vitamins or minerals or general nutrition, tumors, environmental factors, and metabolic disorders such as diabetes mellitus. The primary impediments to acute wound healing are hypoxia, infection, wound debris, and anti-inflammatory medications. The molecular events in the wound healing process of acute, chronic and burn wounds continues to be studied and exhibits an extremely complex array of biochemical events imposing a regulated cascade of inter and intra cellular events. A rapidly growing field of wound healing research is centered around cellular growth factors and the use of these factors for the treatment of wounds. The biochemical response at the cellular level is a process involving intricate interactions among different cell functions which include energy production, structural proteins, growth factors, and proteinases. The treatment of wounds with known cellular growth factors has the potential ability to help heal wounds by stimulating the cellular processes involved in angiogenesis, cellular proliferation, regulating the production and degradation of the extracellular matrix, and being the signal for attracting the inflammatory cells and fibroblasts. Obviously, this complexity requires a plethora of biochemical reactions to provide the functions necessary to accomplish healing of the wound and is not completely understood at this point.

One emerging area of research is the metabolic effect of the alpha keto acids on wound healing. U.S. Pat. No. 6,329,343 discloses the use of a composition of salts of pyruvic acid and/or salts of pyruvic acid and alpha keto glutaric acid, a mixture of fatty acids, and an effective amount of an antibacterial agent as a bioadhesive antibacterial wound healing composition.

Several strategies have been employed to combat the significant infectious complication rates associated with wounds. However, to-date, these strategies have been mainly limited to improved surgical asepsis, surgical technique, and administrative regimens of peri-operative systemic antibiotics and local antibiotic irrigation procedures which have not been well defined. New approaches are emerging in the clinic, including vacuum-sealed dressings, transparent film dressings, irrigation with antimicrobial agents, use of the port and cap, use of new agents such as deuteroporphyrin, gamma interferon (IFN-γ), silver sulfadiazone water soluble gel, geomagnetic therapy, and natural remedies such as milliacynic oil and lysozyme. Unfortunately, few of these innovations have made a major impact on infection and fatality rates and have been shown to have cellular toxicity issues. Most new approaches involve delivery of antimicrobial compounds, to which many wound pathogens are resistant, in some form of salve or in dressings. These treatments lend themselves to continued production of antibiotic resistant bacteria which will negatively affect future therapies against resistive bacteria such as Methicillin-Resistant *Staphylococcus aureus* (MRSA), Vancomycin-resistant enterococci (VRE) and *Acinetobacter baumanni*. *A baumannii* accounts for 6% of Gram-negative infections in intensive care facilities in the USA, with mortality rates as high as 54% having been reported. Isolation of MDR *Acinetobacter* soared from 6.7% in 1993 to 29.9% by 2004, emphasizing the need for newer and better drugs. Out of 1,040 antibiotics tested only 20 (1.92%) exhibited significant antimicrobial activity and only five compounds exhibited activity against the more resistant BAA-1605 *A. baumanni*. Today, MRSA and *C. difficile* are the leading causes of nosocomial infection in most parts of the world. In 2003, *S. aureus* was the leading pathogen associated with skin and soft tissue infections. In the last 20 years, MRSA has moved from an exclusively hospital-acquired pathogen (HA-MRSA) to another type known as a community-acquired pathogen, CA-MRSA. In fact, it has been stated that topical application of antibiotic solutions for lower-limb open fracture wounds offers no advantage over the use of a non sterile soap and may increase the risk of wound-healing problems.

Wound healing and "good" care of wounds has been synonymous with topical prevention and management of microbial contamination. Today's primary therapy involves the use of either topical application of antiseptics or systemic and topical use of antibiotics. The general perspective is that topical application of antibiotics to wounds has no advantages over the use of other antiseptic methods and may increase the risk of wound-healing by producing a sovereign bacteria that is resistant within the wound. The use of silver-based dressings for therapy against infections are widely used in chronic wound and burn therapy. There are several of these commercially available such as Acticoatt™, Aquacels Age®, Contreet® Foam, PolyMem® Silver, Urgotul® SSD). These silver containing dressings do not kill spores or biofilms and require long exposure times that may become cytotoxic over time. The major cause of sepsis in burn wounds, Aspergillus niger has a 70% fatality and is not susceptible to silver compounds.

The cytotoxic effect would explain, in part, the clinical observation of delayed wound healing or inhibition of wound epithelialization after the use of certain topical silver dressings.

There are a myriad of solutions available that claim to kill 99.9% of MRSA and other vegetative bacteria and some spores on surfaces and skin (e.g., hand sanitizers). Therefore, these solutions leave one viable bacterium, or spore, in a thousand or a thousand viable bacteria, or spores, in a million after treatment. However, contaminated surfaces can contain millions of bacteria, some of which can be contained within complex matrices such as blood drops, thus making them difficult to kill. Other types of bacteria, such as *Bacillus subtilis*, form biofilms on surfaces of endoscopes and other medical devices for insertion into the body, which affects the kill efficacy of most disinfectants. These low level disinfectants, often called sanitizers, that claim to kill 99.9% of the bacteria present will not completely kill all bacteria which are present in higher populations (colonized), contained within a complex matrix, or existing as a biofilm.

There are currently several topical antiseptics on the market that are used to diminish the growth of bacterial infections in wounds. Most antiseptics are not suitable for open wounds because they may impede wound healing by direct cytotoxic effects to keratinocytes and fibroblasts. In general, current topical antiseptics have limited bactericidal effect (e.g., 3 log reduction in 30 minute exposure) and nearly all have some cytotoxicity effect which varies with concentration and application time.

There are primarily five high level disinfectants/sterilants in use today. These include glutaraldehyde, orthopthalaldehyde, hypochlorite, hydrogen peroxide, and peracetic acid. The aldehydes are highly toxic and take a very long time to affect a >99.9999% (or 6 log kill). The most successful high level disinfectants used today are oxidizers such as hypochlorites, hydrogen peroxide and peracetic acid. The reactive advantage for disinfection by oxidation is the non-specific free radical damage to all components of the microbe, including proteins, lipids, and DNA. Therefore, microbial resistance to oxidation at high enough solution concentration is virtually non-existent. Safe and non-toxic concentrations of hydrogen peroxide are not capable of killing spores or high populations of microbes. Hypochlorous acid, which is formed by PMN by myeloperoxidase-mediated peroxidation of chloride ions, is easily neutralized at physiological pH by nitrite, a major end-product of cellular nitric oxide (NO) metabolism, and its bactericidal effects subsequently diminished and it is not as effective as silver sulfadiazine, a common topical wound sanitizer. However, it appears that hypochlorous acid does not inhibit wound healing at the concentrations for the effective biocidal levels used. That may be because it is a natural compound found in the inflammatory phase of wound healing. Peracetic acid is used mainly in the food industry, where it is applied as a cleanser and as a disinfectant. Since the early 1950's, acetic acid was applied for bacteria and fungi removal from fruits and vegetables. It was also used for the disinfection of recycled rinsing water for foodstuffs. Nowadays peracetic acid is applied for the disinfection of medical supplies and to prevent biofilm formation in pulp industries. It can be applied during water purification as a disinfectant and for plumbing disinfection. Peracetic acid is produced by a reaction between hydrogen peroxide and acetic acid or it can also be produced by oxidation of acethaldehyde. Peracetic acid is a very powerful oxidant; the oxidation potential outranges that of chlorine and chlorine dioxide. Peracetic acid has not been tested in wound healing. However, it is not known to be involved in any significant cellular metabolism and is typically produced with toxic sulfuric acid catalyst. Thus, many conventional topical wound sanitizers have various limitations.

As stated above, a drawback of the peroxyacid-based chemical disinfectants is their inherent lack of stability, which poses a challenge for shelf-life when used for long term applications. Thus, a need exists for a peracid-based disinfectant, which is an effective broad spectrum antimicrobial, is in an easily removable homogenous antimicrobial coating composition providing both short-term and extended long-term antimicrobial efficacy after application to a surface or a wound.

In addition, there is a continuing need for new topical wound sanitizers, healers or both, and in particular there is a need to develop peroxyacids that are effective sporocides, bactericids and virucides for wounds which are easy to handle and store. Moreover, there is a need for peroxyacids that are easy to handle and store and that have a low corrosive nature. It is therefore desirable to develop a sanitizer that does not decompose rapidly and violently and that can be used as a topical wound sanitizer or as an antimicrobial coating.

The present invention is directed toward overcoming one or more of the problems discussed above.

SUMMARY

Some aspects of the invention provide methods for treating a wound on a subject comprising contacting the wound with a therapeutically effective amount of a composition comprising α-keto peracid and a non-alpha keto peroxyacid. In some aspects, the present invention also relates to peroxyacid compositions and mixtures thereof, as well as methods for making and using peroxyacid compositions and mixtures thereof.

In some aspects the invention also relates to methods for continuous preparation of a peroxyacid composition. The preparation method includes a preliminary stage, a mixing stage, and a main reaction stage.

Some particular embodiments relate to a method for preparing a disinfectant cleansing solution containing a peroxyacid and an α-keto peracid, which is superior in sterilizing, cleansing or disinfecting medical devices and is highly stable.

In some embodiments, the α-keto peracid comprises peroxy 2-oxo monocarboxylic acid. Still in other embodiments, the α-keto peracid comprises peroxy 2-oxo dicarboxylic acid.

In some particular embodiments, the α-keto peracid comprises pyruvate peracid, peroxy 2-oxo butyric acid, peroxy 2-oxo valeric acid, peroxy 2-oxo glutaric acid, or a mixture thereof.

In some particular embodiments, the peroxyacid composition comprises peroxyformic, peroxyacetic, peroxypropionic, peroxysuccinic acid, peroxymalonic acid, peroxybutanoic, peroxypentanoic, peroxyhexanoic, peroxyheptanoic, peroxyoctanoic, peroxynonanoic, peroxydecanoic, peroxylactic, peroxymaleic, peroxyascorbic, peroxyhydroxyacetic, peroxyoxalic, peroxymalonic, peroxysuccinc, peroxyglutaric, peroxyadipic, peroxypimelic, peroxysubric acid and mixtures thereof.

Yet in other embodiments, the composition further comprises hydrogen peroxide.

The combination of the peracids and α-keto peracids produces a synergistic effect, providing a much more potent biocide than can be obtained by using these components separately. In addition, the combination can kill high levels of bacteria and spores in biofilms and in high protein environments. Furthermore, the combination has low corrosivity and presents lower cellular toxicity issues.

The amount of α-keto peracid in the composition can vary depending on a variety of factors including the α-keto peracid, type of wound to be treated, the amount of infection, etc.

The amount of peracid in the composition can vary depending on a variety of factors including the peracid, type of wound to be treated, the amount of infection, etc.

Peracids (peroxycarboxylic or percarboxylic) acids generally have the formula $R(CO_3H)n$, where, for example, R is an alkyl, arylalkyl, cycloalkyl, aromatic, or heterocyclic group, and n is one, two, or three, and named by prefixing the parent acid with peroxy. The R group can be saturated or unsaturated as well as substituted or unsubstituted. Peroxycarboxylic acids can be made by the direct action of an oxidizing agent on a carboxylic acid, by autoxidation of aldehydes, or from acid chlorides, or carboxylic anhydrides with hydrogen or sodium peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, or the peroxyacids of their branched chain isomers, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof. In some embodiments, the compositions of the invention utilize a combination of several different peroxycarboxylic acids. For example, in some embodiments, the composition includes one or more C1 to C4 peroxycarboxylic acids and one or more C5 to C11 peroxycarboxylic acids. Especially preferred is an embodiment in which the peroxycarboxylic acid is peracetic acid (C2), peroxy propionic acid (C3), peroxybutanoic acid (C4), peroxisuccinic and peroxymalonic acid. It should be noted that both the peroxysuccinic and peroxymalonic acid may come from the alpha-keto dicarboxylic acids. Furthermore, because these acids exist in the Krebs cycle they are metabolically active.

In some embodiments, the compositions and methods of the present invention include peroxyacetic acid. Peroxyacetic (or peracetic) acid is a peroxycarboxylic acid having the formula: $CH_3COOOOH$. Generally, peroxyacetic acid is a liquid having an acrid odor at higher concentrations and is freely soluble in water, alcohol, ether, and sulfuric acid.

In some embodiments, the compositions and methods of the present invention include peroxyoctanoic acid, peroxynonanoic acid, or peroxyheptanoic acid, preferably peroxyoctanoic acid. Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof.

Methods of the invention can be used to treat a wide variety of wounds including, but not limited to, a surgical wound, battle wound, accidental wound, thermal burn wound, chemical burn wound, chronic wound, decubitus ulcer, foot ulcer, venous ulcer, laser treatment wound, sunburn, and an abrasion.

Still in other embodiments, the composition is formulated as a gel, a liquid, lotion, skin patch, irrigation gel, a liquid, lotion, skin patch, a spray, application granules, or a combination thereof.

Methods of the invention can be used to treat a wide variety of wounds including, but not limited to, a surgical wound, battle wound, accidental wound, thermal burn wound, chemical burn wound, chronic wound, decubitus ulcer, foot ulcer, venous ulcer, laser treatment wound, sunburn, and an abrasion. Typically, the composition is applied to the wound at least once a day initially.

Compositions of the invention can also comprise a corresponding α-keto carboxylic acid of the α-keto peracid.

In some particular embodiments, the α-keto peracid is of the formula:

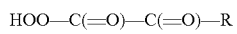

where R is alkyl.

Within these embodiments, in some instances, R is C1-C20 alkyl, often R is C1-C10 alkyl. In some cases, R is selected from the group consisting of methyl, ethyl, isopropyl, propyl, butyl, isobutyl, sec-butyl, pentyl, isopentyl, neopentyl, and n-hexyl.

Other aspects of the invention provide methods for treating a wound infection in a subject comprising contacting the infected wound in the subject with a therapeutically effective amount of a composition comprising α-keto peracid or a salt thereof.

In some embodiments, the α-keto peracid comprises pyruvate peracid, peroxy 2-oxo butyric acid, peroxy 2-oxo valeric acid, peroxy 2-oxo glutaric acid, or a mixture thereof.

Composition can further comprise hydrogen peroxide.

Typically, the composition comprises at least 0.01 mmol/L of α-keto peracid.

Methods of the invention can be used to treat surgical wound, battle wound, accidental wound, thermal burn wound, chemical burn wound, chronic wound, decubitus ulcer, foot ulcer, venous ulcer, laser treatment wound, sunburn, and/or an abrasion.

Generally, the composition is applied to the infected wound at least once, often at least twice a day initially.

Various modifications and additions can be made to the embodiments discussed without departing from the scope of the invention. For example, while the embodiments described above refer to particular features, the scope of this invention also included embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings.

FIG. 4A shows H&E stained cross-sectional derma image of diabetic mouse VERIOX (2.5 mg/kg) treated wound with a well-defined granulation layer of 500 μm at 6 days; FIG. 4B shows H&E stained cross-sectional derma image of diabetic mouse control wound with a diffuse granulation layer of 225 μm at 12 days.

FIGS. 5A and 5B illustrate a graph showing the synergistic effect of the composition comprising the α-keto and the non α-keto peracids for killing biofilms and microbe comprising bacterial spores, mycobacteria, gram-negative bacteria, vegetative gram-positive bacteria, fungus, or a combination thereof.

DETAILED DESCRIPTION

Figure 1:
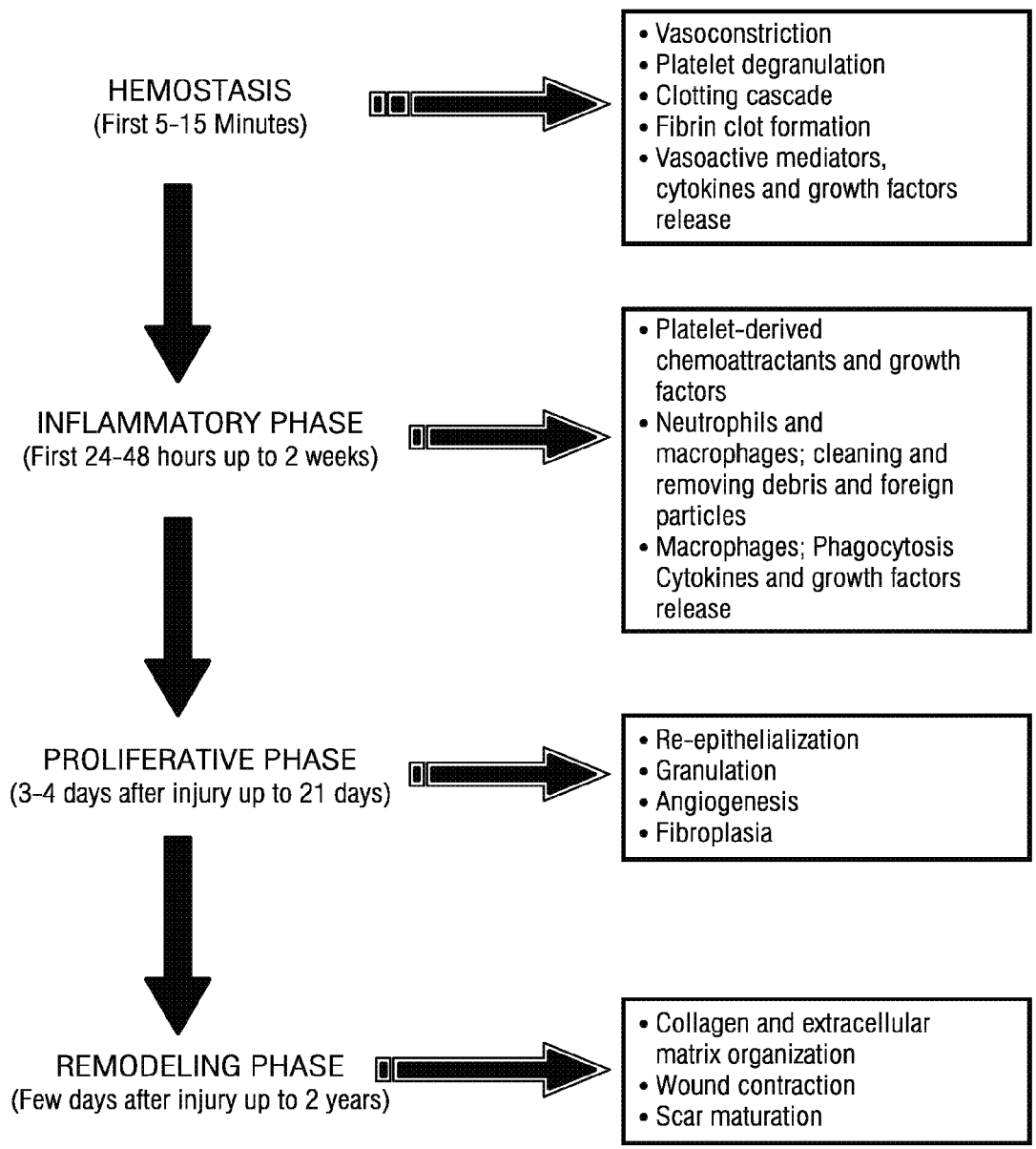
FIG. 1 is a graphic illustration of phases of wound healing process.
Figure 2:
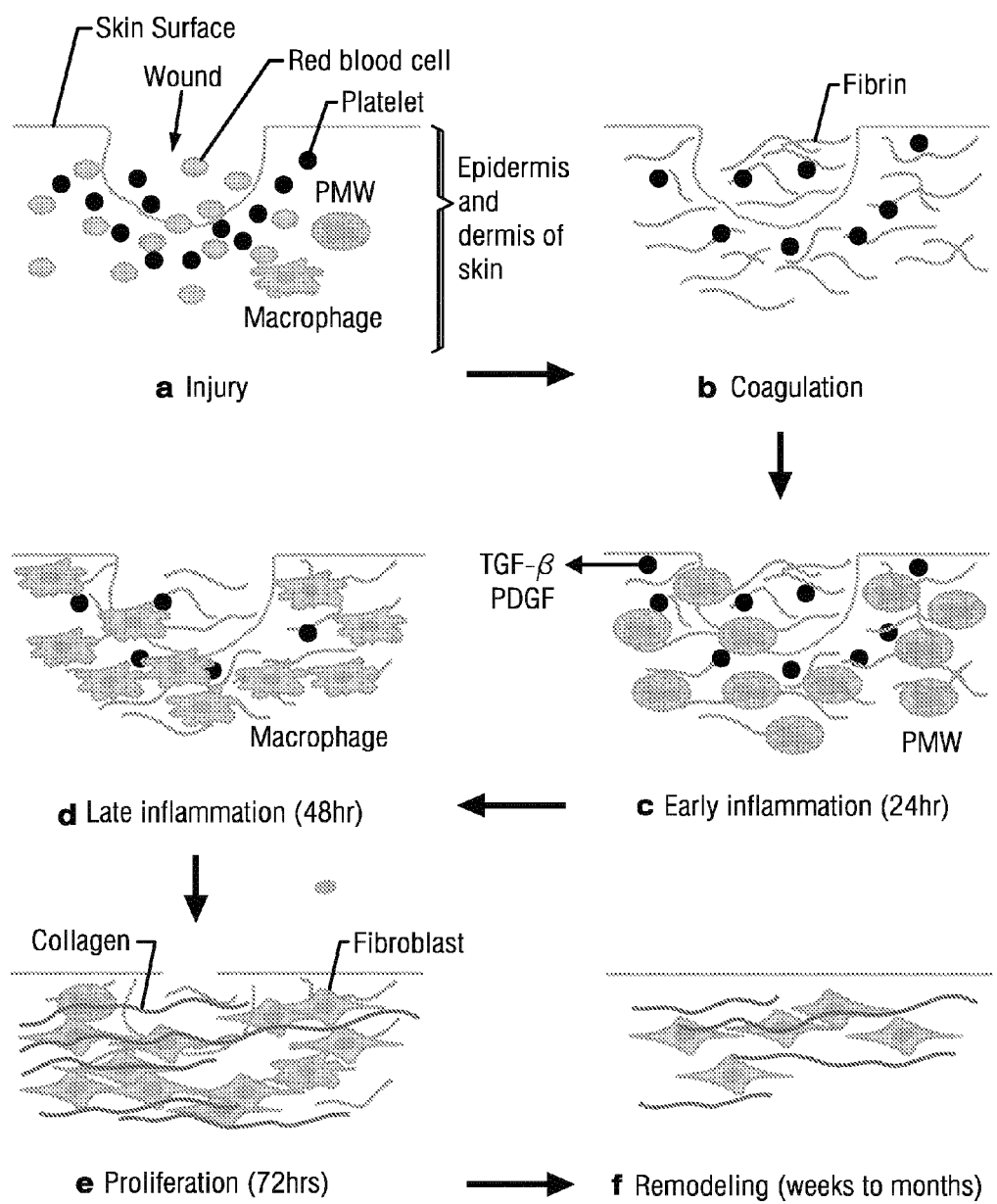
FIG. 2 is a schematic illustration of inflammatory phase of wound healing.
Figure 3:
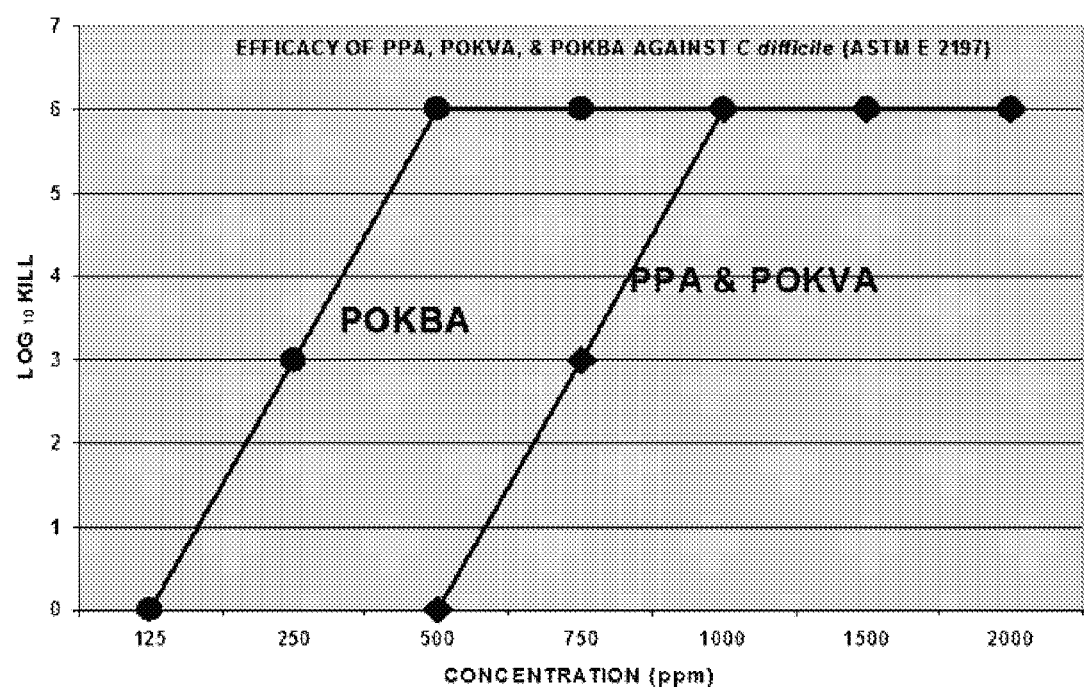
FIG. 3 is a graph showing the biocidal efficacy of a peroxypyruvic acid solution.
Figure 4A:
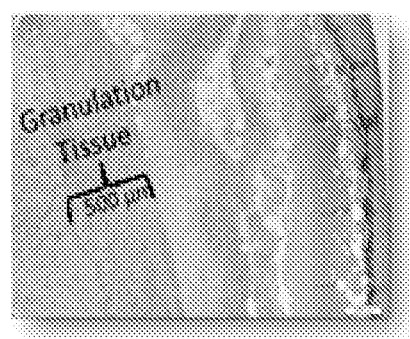
FIGS. 4A and 4B are graphic illustrations of the peroxypyruvic acid healing of diabetic mouse wounds.
Figure 4B:
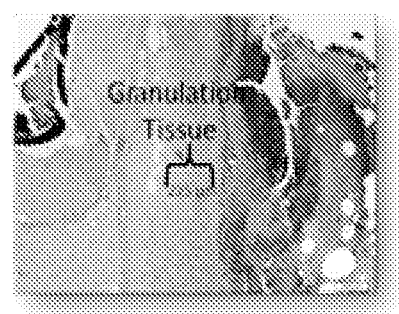
Figure 6:
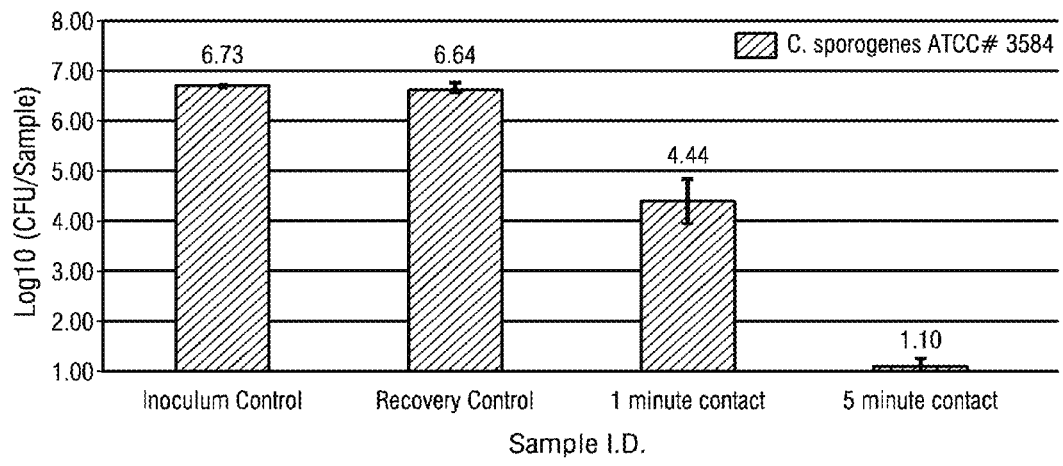
FIG. 6 is graph showing the sporicidal efficacy of the composition of claim 1.
Figure 7:
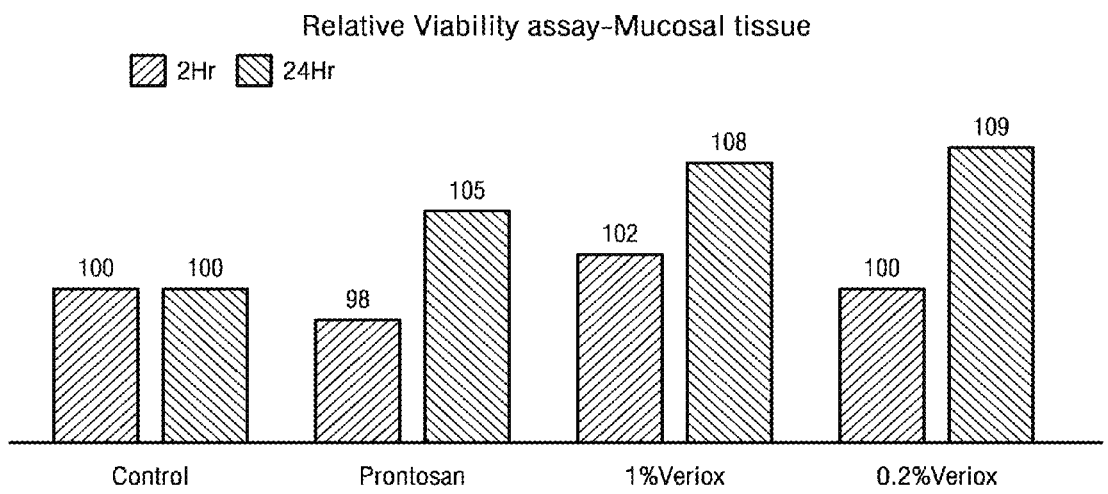
FIG. 7 depicts another graph of the sporicidal effect of the composition of claim 1.

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers expressing quantities of ingredients, dimensions reaction conditions and so forth used in the specification and claims are to be understood as being modified in all instances by the term "about."

In this application and the claims, the use of the singular includes the plural unless specifically stated otherwise. In addition, use of "or" means "and/or" unless stated otherwise. Moreover, the use of the term "including," as well as other forms, such as "includes" and "included," is not limiting. Also, terms such as "element" or "component" encompass both elements and components comprising one unit and elements and components that comprise more than one unit unless specifically stated otherwise.

Some aspects of the invention provide methods for producing non α-keto peracids. As used herein, the terms non α-keto peracid, non α-keto peroxyacid, peracid, peroxycarboxylic acid and peroxyacid are used interchangeably herein and refer to a compounds having an acidic OOH group. A non α-keto peracid may include peroxy acid (often spelled as one word, peroxyacid, and sometimes called peracid), which is an acid containing an acidic —OOH group.

Unless specified, it is not intended that the scope of the invention be limited to the specific values recited when defining a range.

In general, peracids are compounds of oxidized form of a base organic acid (generally a carboxylic acid) that exist in equilibrium with an oxidizer (generally hydrogen peroxide) and water, as shown in scheme 1. One species of peracid with superior antimicrobial properties are peroxy alpha-keto acid (PKCA) compounds (see U.S. Patent Application Publication No. 2010/0261792). PKCA compounds would generally be composed of an alpha-keto carboxylic acid, the anion of that alpha-keto acid, a buffer, and hydrogen peroxide, and the oxidized form of the carboxylic acid. A peroxy pyruvate acid (PPA), for example, may be in equilibrium with pyruvic acid, acetic acid and peracetic acid, as shown in scheme 2 and 3. Peracids may be oxidized from other carboxylic acids, e.g. citric acid, succinic acid, short chain fatty acids, and etc.

Scheme 1

"Biofilm" refers to a structured community of microorganisms encapsulated within a self-developed polymeric matrix and adherent to a living or inert surface. "Drying" refers to a process by which the inert solvent or any other liquid present in the formulation is removed by evaporation.

"Disinfectant" as used herein is a chemical that kills 99.9% of the specific test microorganisms in 10 minutes under the conditions of the test. (Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2)).

"Sterilzation" or "sterilant" as used herein refers to the inactivation of all bio-contamination.

"Locus" as used herein, comprises part or all of a target surface suitable to be coated.

Scheme 2

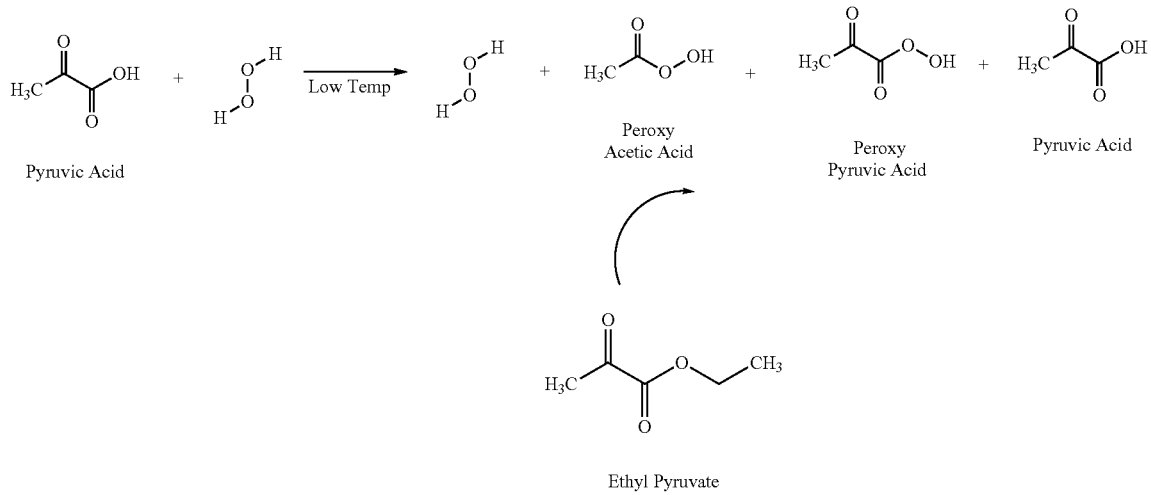

For clarity, terms used herein are to be understood as described herein or as such term would be understood by one of ordinary skill in the art of the invention. Additional explanation of certain terms used herein, are provided below:

"wt %" refers to the weight percent relative to the total weight of the solution or dispersion.

"Microorganism" is meant to include any organism comprised of the phylogenetic domains of bacteria and archaea, as well as unicellular (e.g., yeasts) and filamentous (e.g., molds) fungi, unicellular and filamentous algae, unicellular and multicellular parasites, viruses, virinos, and viroids.

"Film-forming agent" or "water soluble or water dispersible coating agent," which may be used interchangeably herein, refer to agents that form a film and are employed to provide protective coating to the surface of interest. These agents are either water soluble or water dispersible. These agents are described in further detail below.

"Antimicrobial agent" as used herein refers to a compound or substance having antimicrobial properties "Biocide," as used herein, refers to a chemical agent, typically broad spectrum, which inactivates or destroys microorganisms. A chemical agent that exhibits the ability to inactivate or destroy microorganisms is described as having "biocidal" activity.

Some methods of the invention include contacting an α-keto carboxylic acid an oxidizing agent without any significant stifling and under conditions sufficient to produce an α-keto peracid and a non α-keto peracid. Typically, the reaction condition comprises non-stirring conditions where a mixture of the α-keto carboxylic acid and the oxidizing agent is simply allow to stand without any stirring. In other embodiments, the reaction conditions comprise stirring conditions, where a mixture of the α-keto carboxylic acid and the oxidizing agent is stirred. As used herein, unless the context requires otherwise, the term "stir" or "stifling" refers to agitating or act of causing a mixing of the reagents by using an external force such as by using a mechanical stirrer, a magnetic stirrer, a shaker, or any other mechanical, electrical, magnetic, or manual force including simply mixing the reagents manually.

Surprisingly and unexpectedly, the present inventors have found that by contacting an α-keto carboxylic acid and an oxidizing agent and letting the mixture stand without any significant mixing, a good yield of the corresponding non α-keto peroxyacid.

It should be noted that the yield of the non α-keto peroxyacid is affected by a variety of reaction conditions and reagents used. One of the factors influencing the yield of non α-keto peroxyacid is the reaction temperature. Generally, the rate of reaction increases as the temperature increases, however, a higher reaction temperature can also increase the yield of side-product(s) and/or decomposition to the non α-keto peroxyacid. Therefore, the reaction temperature is typically kept at about 0° C. or below, often at about 10° C. or below, and more often at about −20° C. or below.

The concentration of the reagents can also affect the rate and the yield of the non α-keto peroxyacid. The initial concentration of the oxidizing agent is generally about 12 M or less, typically about 7 M or less, and often about 1 M or less.

The reaction time can also affect the yield of non α-keto peroxyacid. Typically the reaction time ranges from about 4 hrs. to about 12 hrs, often from about 6 hrs. to about 8 hrs., and more often from about 10 hrs. to about 12 hrs. It should be noted however, that the time of reaction may differ based on whether or not the stirring or non-stirring method is used.

Methods of the invention are applicable to a wide variety of α-keto carboxylic acids. In fact, generally any α-keto carboxylic acid can be used as long as any reactive functional group within the α-keto carboxylic acid is properly protected. Suitable protection groups for various chemical reactions are well known to one skilled in the art. See, for example, Protective Groups in Organic Synthesis, 3rd edition, T. W. Greene and P. G. M. Wuts, John Wiley & Sons, New York, 1999; Smith and March, Advanced Organic Chemistry, 5th ed., John Wiley & Sons, New York, N.Y., 2001; and Harrison and Harrison et al., Compendium of Synthetic Organic Methods, Vols. 1-8 (John Wiley and Sons, 1971-1996), which are incorporated herein by reference in their entirety. Exemplary α-keto carboxylic acids include, but are not limited to, pyruvic acid, α-keto butyric acid, α-keto valeric acid, α-keto glutaric acid, 2-oxo cylopental acetic acid, etc.

Exemplary oxidizing agents that are useful in methods of the invention include, but are not limited to, hydrogen peroxide, barium peroxide, sodium carbonate peroxide, calcium peroxide, sodium perborate, lithium peroxide, magnesium peroxide strontium peroxide, zinc peroxide, potassium superoxide, and the like.

When describing a chemical reaction, the terms "treating," "contacting," and "reacting" are used interchangeably herein, and refer to adding two or more reagents under appropriate conditions to produce the indicated and/or the desired product. It should be appreciated that the reaction which produces the indicated and/or the desired product may not necessarily result directly from the combination of reagents which were initially added, i.e., there may be one or more intermediates which are produced in the mixture which ultimately leads to the formation of the indicated and/or the desired product.

The reaction is generally conducted in an aqueous solution. Other solvents, such as an organic solvent can also be used in addition to or in place of the aqueous solution. Because it is inexpensive and commercially available in an aqueous solution, typically hydrogen peroxide is used as an oxidizing agent.

The ratio of oxidizing agent to α-keto carboxylic acid typically ranges from about 0.5:1 to about 2:1, often about 2:1 to about 6:1.

While various reaction parameters are disclosed herein, it should be appreciated that the scope of the invention is not limited to these particular reaction parameters.

Various embodiments of the disclosure could also include permutations of the various elements recited in the claims as if each dependent claim was a multiple dependent claim incorporating the limitations of each of the preceding dependent claims as well as the independent claims Such permutations are expressly within the scope of this disclosure.

Some aspects of the invention disclose a process for forming a stable aqueous composition containing a non α-keto peroxy acid.

Environmental concerns about the effects of certain chemicals on the upper atmosphere have led to some unease about the widespread use of certain disinfectants. Hydrogen peroxide, peracetic acid, persulfates and peroxyhydrates, such as sodium perborate are well known as disinfectant compounds but are highly corrosive and sometimes hard to handle and/or store.

It is therefore particularly desirable that an antimicrobial containing a non α-keto peroxy acid be available for use as a single, stable gel or a viscous solution (sol), although a solid would be satisfactory if it were biodegradable, easily soluble in water, and did not contain significant inorganic dissolved solids such as are provided by sodium persulfate or sodium perborate. It is also desirable for the antimicrobial to have less odor, be non-corrosive and promote wound healing.

The embodiments disclosed herein overcome the problems of the prior art by providing an aqueous composition comprising stable sols, gels and solids of C2 to C6 peroxycarboxylic acids. In some embodiments, the compositions of the invention provide a combination of several different peroxycarboxylic acids. For example, in some embodiments, the composition includes one or more C1 to C4 peroxycarboxylic acids and one or more C5 to C11 peroxycarboxylic acids. Especially preferred is an embodiment in which the peroxycarboxylic acid is peracetic acid (C2) peroxy propionic acid (C3) peroxybutanoic acid (C4), peroxysuccinic and peroxymalonic acid. Such compositions form carriers for delivering peroxycarboxylic acids for applications related to high level disinfectants/sterilants of vegetative bacteria, spores and biofilms. The compositions are particularly useful for killing vegetative bacteria and spores at the level acceptable to be called disinfectants. Unlike most peroxy carboxylic compounds, it was discovered that the non α-keto peroxyacid compounds in combination with keto peroxyacids do not require an acid catalyst for efficient synthesis and are effective against biofilms. Without the need for a toxic catalyst for synthesis, the mixture of the embodiments disclosed herein typically contains water, the α-keto acid, hydrogen peroxide, the peroxy α-keto acid and the peroxy non α-keto acid, all of which work synergistically and are beneficial to healing of a wound. Many of the parent compounds (i.e., the corresponding carboxylic acids) of the embodiments disclosed herein are present within nearly all living cells and play significant roles in essential cellular metabolism. For example, the parent carboxylic acid compounds of peroxypyruvic acid, peroxy oxaloacetate, peroxy α-keto glutarate, are key compounds within the TCA cycle, the predominant energy producer for cellular metabolism. The parent compound of peroxy alpha keto butyric acid, i.e., alpha keto butyric acid, is involved in the metabolic production of succinyl-CoA which is also used in the TCA cycle and thus contributes to cellular energy production. Alpha keto valeric acid, the parent compound of peroxy alpha keto valeric acid, is an intermediate in protein synthesis and the biosynthesis of the amino acids such as leucine and valine. Alpha keto valeric acid is involved in gluconeogenesis in cells. Pyruvate is involved in producing energy for hypoxic cells during wound healing through glycolysis. The potential harmful effects of the ROS can be mediated by α-keto acids. In addition, pyruvate is involved in protecting DNA during hypoxia and is an indirect metabolic contributor to collagen deposition and angiogenesis in wound healing. Moreover, pyruvic acid accelerates the debridement of the dead skin in both wounds and burns.

Additionally, it was particularly unexpected that stable peracid compositions could be prepared, since peracids are very strong oxidizing agents even at a pH of 2 to 8 because the water soluble peracids are decomposing to form free radicals.

For the purpose of this invention a "stable" peracid composition is one which maintains sufficient physical properties and active oxygen content long enough to be useful, about twelve months.

Any C2 to C6 percarboxylic acid which is water soluble may be incorporated into the compositions. Examples, include peracetic acid, perproprionic acid, perbutyric acid, pervaleric acid, percaproic acid, and the like and derivatives thereof.

Studies show that many widely used wound antiseptics have undesired cytotoxicity, and while some do kill bacteria at a sufficient level, they often do not promote a relatively fast wound healing. In many cases, irrigation of open fracture wounds with an antibiotic solution offers no significant advantages over the use of a non sterile soap solution and may in fact increase wound-healing problems.

To be useful, topical antiseptics should be toxic to bacteria but should have no significant toxicity to underlying tissues, and ideally, they should also preserve or enhance host defense against infection. The present invention provides a method for treating wounds including, but not limited to, surgical, traumatic, chronic and burn wounds. Methods of the invention promote wound healing and typically rapidly kill high levels of viruses, vegetative bacteria, fungi, mycobacteria and spores. Unlike many conventional antiseptics available today, compositions and methods of the invention eliminate bacteria, enhance body's defense system, and enhance the healing process. Without being bound by any theory, it is believed that these benefits are achieved at least in part by the synergistic effect of the parent α-keto acids working together with resultant alpha-keto peracid and a non-alpha keto peroxyacid. It is believed that the synergetic effect results in energy generation and serves as intermediates in the generation of other biomolecules that are useful in wound healing.

In addition, the combination of the peracids and α-keto peracids disclosed in the present embodiments can kill high levels of bacteria and spores in biofilms and in high protein environments without being corrosive and having virtually no cellular toxicity issues.

It should be appreciated that because the stability of α-keto peracids and non α-keto peracids are often limited, in many instances compositions of the invention can include the presence of the parent carboxylic acid. As used herein, the term "parent carboxylic acid" refers to the corresponding carboxylic acid in which the α-keto peracid is derived from or is degraded into under a typical storage or production conditions. In some embodiments, the parent carboxylic acid is present in the composition of the invention in an amount of about 120.4 mM or less, typically, about 12.4 mM or less, more typically, about 6.2 mM or less, often about 2.5 mM or less, more often, about 1.2 mM or less, still more often about 0.62 mM or less, yet more often about 0.31 mM or less, and most often about 0.062 mM or less.

Still in other embodiments, compositions of the invention can include hydrogen peroxide. Typically, the amount of hydrogen peroxide present in the wound healing compositions of the invention is about 715 mM or less, typically about 71.5 mM or less, more typically about 35.8 mM or less, often about 14.3 mM or less, more often about 7.2 mM or less, still more often about 3.6 mM or less, yet more often about 1.8 mM or less, and most often about 0.35 mM or less.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The following examples are provided for illustrative purposes only and are not intended to limit the scope of the invention.

Example 1

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A method comprising:
   contacting at least one first α-keto carboxylic acid with an oxidizing agent to form a mixture, and stirring the mixture at a temperature from −20° C. to 0° C. to produce non-α-keto peracids comprising at least one first percarboxylic acid.

2. The method of claim 1 further comprising formulating the non-α-keto peracids in a gel, a lotion, or an irrigation gel.

3. The method of claim 1 further comprising formulating the non-α-keto peracids in a liquid, a spray, or application granules.

4. The method of claim 1 further comprising incorporating the non-α-keto peracids in a skin patch.

5. The method of claim 1, wherein the oxidizing agent is at least one agent selected from the group consisting of hydrogen peroxide, barium peroxide, sodium carbonate peroxide, calcium peroxide, sodium perborate, lithium peroxide, magnesium peroxide, strontium peroxide, zinc peroxide, potassium superoxide.

6. The method of claim 5, wherein the oxidizing agent is hydrogen peroxide.

7. The method of claim 1, wherein the at least one first α-keto carboxylic acid is selected such that the at least one first peroxycarboxylic acid is selected from the group consisting of peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, the peroxyacids of the branched chain isomers of the foregoing.

8. A method comprising contacting pyruvic acid with an oxidizing agent to form a mixture, and stirring the mixture at a temperature from −20° C. to 0° C.

9. The method of claim 8, wherein the oxidizing agent and the pyruvic acid are at a ratio of 0.5:1 to 6:1.

10. The method of claim 9, wherein the ratio is 2:1.

11. The method of claim 10, wherein the method comprises a reaction time of 4 hours to 12 hours.

12. The method of claim 11, wherein the reaction time is 10 hours to 12 hours.

13. The method of claim 1, wherein the oxidizing agent and the α-keto carboxylic acid are at a ratio of 0.5:1 to 6:1.

14. The method of claim 13, wherein the ratio is 2:1.

15. The method of claim 14, wherein the method comprises a reaction time of 4 hours to 12 hours.

16. The method of claim 15, wherein the reaction time is 10 hours to 12 hours.

17. The method of claim 1, wherein the method comprises a reaction time of 4 hours to 12 hours.

18. The method of claim 17, wherein the reaction time is 10 hours to 12 hours.

19. The method of claim 1, wherein contacting further comprises contacting at least one second α-keto carboxylic acid with the oxidizer, and the mixture comprises the at least one first α-keto carboxylic acid, the at least one second carboxylic acid, and the oxidizer, and the non-α-keto peracids further comprise at least one second percarboxylic acid.

20. The method of claim 19, wherein the at least one first α-keto carboxylic acid are chosen such that the at least one first peroxycarboxylic acid is selected from the group consisting of peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, and the branched chain isomers of the foregoing, and the at least one second α-keto carboxylic acid are chosen such that the at least one second peroxycarboxylic acid is selected from the group consisting of peroxylactic acid, peroxymaleic acid, peroxyascorbic acid, peroxyoxalic acid, peroxymalonic acid, peroxyglutaric acid, peroxyadipic acid, peroxypimelic acid, and peroxysuberic acid.

21. The method of claim 20, wherein the at least one second peroxycarboxylic acid is selected from the group consisting of peroxylactic acid, peroxyascorbic acid, peroxyglutaric acid, peroxypimelic acid, and peroxysuberic acid.

22. The method of claim 20, wherein the at least one second peroxycarboxylic acid comprises peroxymaleic acid.

* * * * *